United States Patent [19]

Klem et al.

[11] Patent Number: 5,723,599
[45] Date of Patent: Mar. 3, 1998

[54] ORGANIC POLYMER REAGENTS FOR SOLID PHASE SYNTHESIS OF OLIGONUCLEOTIDES

[75] Inventors: Robert E. Klem, San Luis Obispo; Timothy A. Riley, Grover City, both of Calif.

[73] Assignee: Genta Incorporated, San Diego, Calif.

[21] Appl. No.: 409,902

[22] Filed: Mar. 22, 1995

Related U.S. Application Data

[63] Continuation of Ser. No. 231,900, Apr. 22, 1994, abandoned, which is a continuation of Ser. No. 781,329, Oct. 18, 1991, abandoned, which is a continuation-in-part of Ser. No. 605,849, Oct. 26, 1990, abandoned.

[51] Int. Cl.$^6$ .................. C07H 21/00; C08F 18/00
[52] U.S. Cl. .............. 536/25.3; 536/25.31; 536/25.32; 536/25.33; 536/25.34; 526/320
[58] Field of Search ................ 526/320; 536/25.3

[56] References Cited

U.S. PATENT DOCUMENTS

| | | | |
|---|---|---|---|
| 3,494,904 | 2/1970 | Waples | 526/320 |
| 3,660,359 | 5/1972 | Labana | 528/45 |
| 4,070,348 | 1/1978 | Kraemer et al. | 426/273 |
| 4,076,921 | 2/1978 | Stol et al. | 526/89 |
| 4,138,383 | 2/1979 | Rembaum et al. | 526/303 |
| 4,552,812 | 11/1985 | Marg et al. | 428/407 |

FOREIGN PATENT DOCUMENTS

| | | |
|---|---|---|
| 0168623 | 12/1981 | Japan. |
| 9401446 | 1/1994 | WIPO. |

OTHER PUBLICATIONS

Ikehara et al. eds., "The Synthesis of Polynucleotides," *Adv. Carbohydrate Chem. and Biochem.*, 36, 135–213 (1979); pp. 135, 204–213 supplied.

Caruthers, "DNA Synthesis for Nonchemists: The Phosphoramidite Method on Silica Supports," Ch. 3 in *Synthesis and Applications of DNA and RNA*, Narang ed., Academic Press, 1987, New York, pp. 47–94; pp. 47 and 52–55 supplied.

*Primary Examiner*—John Kight
*Assistant Examiner*—L. Eric Crane
*Attorney, Agent, or Firm*—Lyon & Lyon

[57] ABSTRACT

Polymeric reagents useful in the solid phase synthesis of oligomers are provided. These polymeric reagents are suitably loaded with nucleosidyl moieties and do not undergo non-specific chain elongation.

21 Claims, 7 Drawing Sheets

Figure 1.

Step 1

Step 2

Step 3

After capping, this material is recycled in Step 1.

```
AGC ACT TTT AAA GAG CCC TTT CCT GGT TGG GTT GAA GGT GTC AGG ACC    928
Ser Thr Phe Lys Glu Pro Phe Pro Gly Trp Val Glu Gly Val Arg Thr
270                 275                 280

ATC GAT AAT GTA CCT GTA TAT TAT GGT AAA GGG AGA TTG AGG TGT ATG    976
Ile Asp Asn Val Pro Val Tyr Tyr Gly Lys Gly Arg Leu Arg Cys Met
285                 290                 295                 300

CTT TGC GGA CCC AGC ACA ATA ATT GAC CTG ATA CCG GCA GAT ATG GTC   1024
Leu Cys Gly Pro Ser Thr Ile Ile Asp Leu Ile Pro Ala Asp Met Val
            305                 310                 315

GTG AAT GCA ACG ATA GTA GCC ATG GTG GCG CAC GCA AAC CAA AGA TAC   1072
Val Asn Ala Thr Ile Val Ala Met Val Ala His Ala Asn Gln Arg Tyr
320                 325                 330

GTA GAG CCG GTG ACA TAC CAT GTG GGA TCT TCA GCG GCG AAT CCA ATG   1120
Val Glu Pro Val Thr Tyr His Val Gly Ser Ser Ala Ala Asn Pro Met
335                 340                 345

AAA CTG AGT GCA TTA CCA GAG ATG GCA CAC CGT TAC TTC ACC AAG AAT   1168
Lys Leu Ser Ala Leu Pro Glu Met Ala His Arg Tyr Phe Thr Lys Asn
350                 355                 360
```

FIGURE 1D

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 18
( B ) TYPE: nucleic acid
( C ) STRANDEDNESS: single
( D ) TOPOLOGY: linear ( x i ) SEQUENCE DESCRIPTION: SEQ ID NO: 1:

GTCTTCCTGC CCCATTGC         1 8

( 2 ) INFORMATION FOR SEQ ID NO: 2:

( i ) SEQUENCE CHARACTERISTICS:
( A ) LENGTH: 15
( B ) TYPE: nucleic acid
( C ) STRANDEDNESS: single
( D ) TOPOLOGY: linear (x i) SEQUENCE DESCRIPTION: SEQ ID NO: 2:

TCTCTAGCAG AGGAA    15

(2) INFORMATION FOR SEQ ID NO: 3:

(i) SEQUENCE CHARACTERISTICS:
      (A) LENGTH: 15
      (B) TYPE: nucleic acid
      (C) STRANDEDNESS: single
      (D) TOPOLOGY: linear    (x i) SEQUENCE DESCRIPTION: SEQ ID NO: 3:

TTCTGAGGCC GTGTA    15

ORGANIC POLYMER REAGENTS FOR SOLID PHASE SYNTHESIS OF OLIGONUCLEOTIDES

This application is a continuation of U.S. Ser. No. 08/231,900, filed Apr. 22, 1994, now abandoned, which is a continuation of U.S. Ser. No. 07/781,329, filed Oct. 13, 1991, now abandoned, which is a continuation-in-part of U.S. Ser. No. 07/605,849, filed Oct. 26, 1990, now abandoned.

BACKGROUND OF THE INVENTION

The present invention is directed to an improved polymeric reagent for the solid phase synthesis of oligomers and methods of synthesizing oligomers using said polymeric reagents.

Methods for the chemical synthesis of oligomers, and in particular, oligomers composed of deoxyribonucleosides or ribonucleosides have been developed. These methods include the phosphotriester method and the phosphite triester method. These syntheses may be conducted in solution, but preferably a solid phase method is employed using a 5'-O-protected nucleoside attached to a solid support.

In the solid phase method, a 5'-O-protected nucleoside is attached to a solid support and an oligomer is synthesized by chain assembly using alternating terminal 5'-deprotection reactions and coupling reactions. In these synthesis methods, excess reagent is added to drive the reaction to completion and unreacted components are removed by washing of the support with appropriate solvent(s). Cycles of deprotection and coupling (including oxidizing and capping steps) are continued until the desired oligomer length is obtained. Then, the oligomer is cleaved from the support, protecting groups are removed, and the deprotected oligomer is purified. (See, in general, Gait, M. S., *Oligonucleotide Synthesis A Practical Approach*, IRL Press (1985)).

Instruments for the solid phase synthesis of oligomers are commercially available. The instructions provided by the manufacturers include preferred solid supports, preferred ratios of reactants and reagents for synthesis and preferred reaction conditions. Solid supports conventionally used in solid phase synthesis of oligomers include controlled pore glass ("CPG"), and silica gel.

Previously used silica gel supports include Fractosil (particle size 65–125μ) which consists of irregularly shaped silica particles. However, Fractosil particles are brittle and tend to form fines which may cause blockages of apparatus such as sintered glass funnels. Moreover, Fractosil has a lower surface area than other supports such as CPG (about 50 m²/g for supports of pore size of about 500 Å versus about 70 to 80 m²/g for CPG), which results in decreased capacity for loading of nucleoside on support. In addition, silica gel supports have a tendency to dissolve in high pH (concentrated ammonium hydroxide) solutions used for oligomer release.

Controlled pore glass has been the conventionally preferred support. CPG is more resistant to the formation of fines than Fractosil and other silica gels and, due to its larger surface area at a given pore size, has increased capacity for loading of nucleoside on support. However, use of CPG has resulted in non-specific binding of oligomer to support after release. In addition, CPG has a tendency to initiate oligomer chains after the first reaction cycle (despite capping) so that a large N-1 peak of truncated oligomer is obtained. Moreover, CPG supports are relatively expensive, costing on the order of about 50 dollars per gram.

Certain aromatic organic polymeric supports such as polystyrene resins have been used for the synthesis of oligomers, but have proved unsatisfactory because of excessive size changes with changes in solvents during synthesis procedures, that is, high swelling followed by subsequent contraction with a change in solvents, and because of absorption of solvent which then is difficult to remove in subsequent steps. In particular, these aromatic organic polymeric organic supports have proved unsuitable for use in closed column systems for oligonucleoside synthesis.

Accordingly, there is a need for a support suitable for use in oligomer synthesis which does not have the above-noted drawbacks of CPG and other conventionally used supports and which is economical cost-wise.

SUMMARY OF THE INVENTION

The present invention is directed to a solid polymeric reagent for the solid phase synthesis of oligomers which comprises a polymeric moiety linked by a linking moiety to a nucleosidyl moiety.

In one aspect, the present invention is directed to a polymeric reagent for solid phase synthesis of oligomers which comprises a non-aromatic organic polymeric moiety linked by a linking moiety to a nucleosidyl moiety. The polymeric moiety has a density such that it is easily suspendible in solvents used in said solid phase synthesis, is stable to contact with strong base, and does not appreciably expand or contract in contact with said solvents. Suitable non-aromatic organic polymeric moieties include copolymers of: (a) polyethylenically unsaturated monomers and monoethylenically unsaturated aliphatic monomers; and (b) polyvinylidene ethylenic monomers and monoethylenically unsaturated monomers.

According to one aspect of the present invention, preferred are polymeric moieties which have a particle size of about 10 to about 200 microns and a pore size of about 60 Å to about 2,000 Å. One preferred class of polymeric reagents comprises polymers having a macroreticular structure characterized by a reticular structure of microscopic channels through its mass and a density less than the same polymer without a reticular structure.

The polymeric reagents of the present invention are particularly advantageous for the solid phase synthesis of oligomers using automated nucleic acid synthesizing instruments. Suitable instruments include those such as the Biosearch Models 8750 and 8800, those sold by Applied Biosystems, Inc. and the like.

The polymeric reagents are particularly suited for use in the processes for oligomer synthesis described in the commonly-assigned, co-pending United States patent application, Ser. No. 07/605,790 for "Improved Process for the Synthesis of Oligomers," filed Oct. 26, 1990, the disclosure of which is incorporated herein by reference.

Among other factors, the present invention is based on our finding that these polymeric reagents are especially suited to the solid phase synthesis of oligomers. These polymeric reagents have a density such that they are easily suspendible in the solvent systems used and exhibit improved fluidization in the reaction vessels of the DNA synthesizer so that the reactants for the reaction steps are quickly mixed and the reactions quickly go to completion. Use of these polymeric reagents as supports also results in decreased non-specific coupling of monomer to support, rather than to the attached nucleoside or growing oligomer chain, and, thus, decreased non-specific chain initiation. Such non-specific chain initiation results in oligomers of N-1 chain length where N represents the intended chain length for the synthesized oligomer. In particular, these polymeric reagents have other advantageous properties which include improved efficiency of rinsing of support during the reactions; stability at high pH which allows efficient release (cleaving) of oligomer from the support without dissolving support; being nonfriable and having improved resistance to attrition so that fewer fines are formed; good loading of monomer to polymeric moiety; and decreased non-specific binding of oligomer to support (i.e. absorption of oligomer by support which occurs during and/or after release of the protected oligomer from the support), all resulting in good coupling efficiency.

Definitions

As used herein, the following terms have the following meanings, unless expressly stated to the contrary:

The term "nucleoside" includes a nucleosidyl moiety or unit and is used interchangeable therewith, and refers to a subunit of a nucleic acid which comprises a 5-carbon sugar and a nitrogen-containing base. The term includes not only units having A, G, C, T and U as their bases, but also analogs and modified forms of the bases. In RNA, the 5-carbon sugar is ribose; in DNA it is a 2'-deoxyribose. The term also includes analogs of such subunits, including modified sugars such as 2'-O-alkylribose.

The term "nucleotide" refers to a subunit of a nucleic acid consisting of a phosphate group, a sugar and a nitrogen containing base. In RNA the sugar is ribose. In DNA, it is a 2-deoxyribose. The term also includes analogs of such subunits.

The terms "nucleotide multimer" refers to a chain of nucleotides linked by internucleoside phosphate linkages or analogs thereof.

An "oligonucleotide" is a nucleotide multimer generally about 3 to about 100 nucleotides in length, but which may be greater than 100 nucleotides in length. They are usually considered to be synthesized from nucleotide monomers.

A "deoxyribooligonucleotide" is an oligonucleotide consisting of deoxyribonucleotide monomers.

A "polynucleotide" refers to a nucleotide multimer generally about 100 nucleotides or more in length. These are usually of biological origin or are obtained by enzymatic means.

A "monomeric unit" refers to a unit of either a nucleotide reagent or a non-nucleotide reagent of the present invention, which the reagent contributes to a polymer.

A "non-nucleotide monomeric unit" refers to a monomeric unit which does not significantly participate in hybridization of an oligomer. Such monomeric units must not, for example, participate in any significant hydrogen bonding with a nucleotide, and optionally include groupings capable of interacting after hybridization of oligomer to the target sequence, e.g. such as cross-linking alkylation, intercalating and chelating agents.

An "oligonucleotide/non-nucleotide multimer" is a multimer generally of synthetic origin having less than 100 nucleotides, but which may contain in excess of 200 nucleotides and which contains one or more non-nucleotide monomeric units.

The term "oligomer" refers to oligonucleotides, nonionic oligonucleoside alkyl- and aryl-phosphonate analogs, alkyl- and aryl phosphonothioate analogs, phosphorothioate or phosphorodithioate analogs of oligonucleotides, phosphoramidate analogs of oligonucleotides, neutral phosphate ester oligonucleotide analogs, such as phosphotriesters and other oligonucleotide analogs and modified oligonucleotides, and also includes nucleotide/non-nucleotide polymers. The term also includes nucleotide/non-nucleotide polymers wherein one or more of the phosphorus group linkages between monomeric units has been replaced by a non-phosphorus linkage such as a formacetal linkage, a morpholino linkage, a sulfamate linkage or a carbamate linkage.

The term "alkyl- or aryl-phosphonate oligomer" refers to nucleotide/non-nucleotide polymers having internucleoside (or intermonomer) phosphorus group linkages wherein at least one alkyl- or aryl- phosphonate linkage replaces a phosphodiester linkage.

The term "methylphosphonate oligomer" (or MP-oligomer") refers to nucleotide oligomers (or nucleotide/non-nucleotide polymer) having internucleoside (or intermonomer) phosphorus group linkages wherein at least one methylphosphonate internucleoside linkage replaces a Phosphodiester internucleoside linkage.

In some of the various oligomer sequences listed herein "p" in, e.g., as in ApA represents a phosphate diester linkage, and "p" in, e.g., as in CpG represents a methylphosphonate linkage. Certain other sequences are depicted without the use of p or p to indicate the type of phosphorus diester linkage. In such occurrences, A as in ATC indicates a phosphate diester linkage between the 3'-carbon of A and the 5' carbon of T, whereas A, as in ATC or ATC indicates a methylphosphonate linkage between the 3'-carbon of A and the 5'-carbon of T or T.

The term "non-adverse conditions" describes conditions (of reaction or synthesis) which do not substantially adversely affect the oligomer skeleton and its sugar and base components, nor the solid support. One skilled in the art can readily identify functionalities, coupling methods, deblocking and deprotection procedures and cleavage conditions which meet these criteria.

The term "deblocking conditions" describes the conditions used to remove the blocking (or protecting) group from the 5"—OH group on a ribose or deoxyribose group.

The term "deprotecting conditions" describes the conditions used to remove the protecting groups from the nucleoside bases.

The term to "cap" or "capping" refers to a step in the reaction cycle in which any 5'-hydroxyl groups of the first nucleoside (of a particular reaction cycle) that failed to condense (i.e. react) with the activated coupling group of the second nucleoside of that reaction cycle) are blocked, rendering them unreactive in further reaction cycles.

The term "loading" refers to the amount of nucleosidyl moiety (or nucleoside) which is coupled or linked (by a linking moiety) to a support or the polymeric moiety of a polymeric reagent of the present invention and is typically expressed in μmoles nucleoside per gram support.

The term "support" refers to a solid particulate material to which a nucleoside is linked and from which an oligomer can be synthesized. Supports used in synthesizing oligomers are typically substantially inert and nonreactive with the reagents used in the synthesis of oligomers and includes a polymeric moiety such as included in a polymeric reagent of the present invention.

The term "non-aromatic organic support" or "non-aromatic organic polymeric moiety" refers to supports or polymeric moieties comprising polymeric chains which contain less than about 10% aromatic residues; however, these supports include supports using aromatic cross-linking reagents such as divinylbenzene. Non-aromatic organic supports exclude supports comprising greater than about 10% aromatic monomeric units within the polymeric chains (as opposed to cross-links between the polymeric chains) and would exclude supports such as polystyrene, poly (substituted styrenes) and polyphenols.

The terms "acrylic polymers" or "acrylic polymeric moieties" and "methacrylic polymers" or "methacrylic polymeric moieties" refer to polymers comprising esters of acrylic acid and methacrylic acid, respectively.

BRIEF DESCRIPTION OF THE DRAWINGS

FIGS. 6a and 6b depict examples of the conjugation partners —X and —Y and resulting conjugation pairs —XY— used in the preparation of the polymeric reagents of the present invention and as depicted in FIGS. 2 to 5.

DETAILED DESCRIPTION OF THE INVENTION

In one aspect, the present invention is directed to a polymeric reagent which is useful as a support in the solid phase synthesis of oligomers. The polymeric reagent comprises a polymeric moiety linked by a linking moiety to a nucleosidyl moiety.

In one aspect, the present invention is directed to polymeric reagents of the general formula:

PM—CP$_1$—LM—CP$_2$—CM—XO-PrNu wherein PM is a polymeric moiety, LM is a linking moiety, CM is a coupling moiety or a direct link, CP$_1$ and CP$_2$ are conjugation pairs; however when CM is a direct link, CP$_2$ is also a direct link; —XO— is a linkage cleavable under non-adverse conditions; and PrNu is a 5'-blocked protected nucleosidyl group attached to —XO— at the 3'-carbon.

Preferred polymeric moieties, linking moieties, nucleosidyl moieties and optional coupling moieties are described below.

Figure 6A:
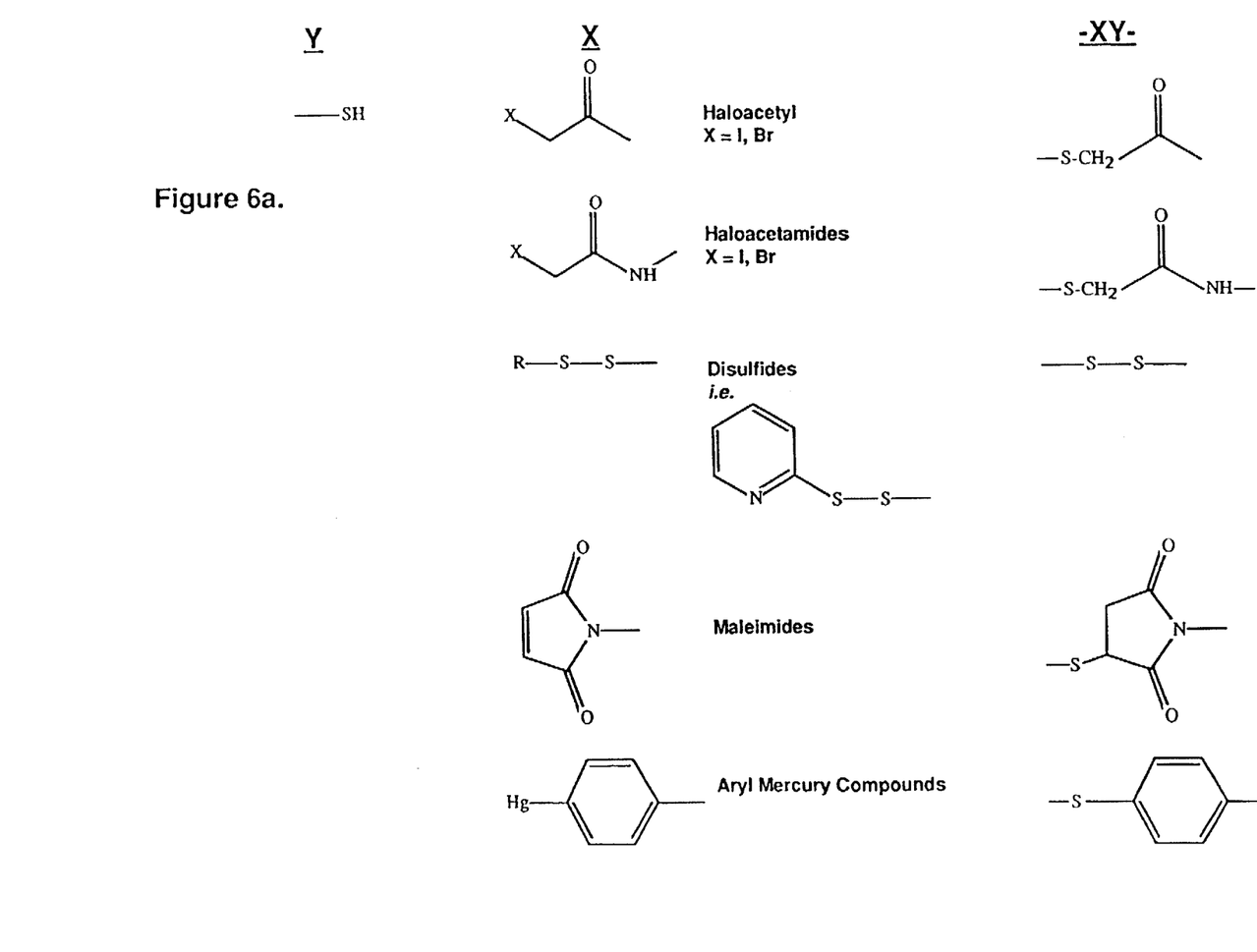

Suitable conjugation pairs include the groups —XY— depicted in FIGS. 6a and 6b. Suitable linkages —XO— (or —OX—) are depicted in 6b where Y comprises —OH.

A. PREFERRED POLYMERIC MOIETIES

Suitable polymeric moieties comprise non-aromatic organic polymers, copolymers or polymeric materials. These non-aromatic organic polymeric moieties have lower bulk density than CPG, and preferably have a density such that it is easily suspendible in the solvents used in the DNA synthesizer, and exhibits excellent fluidization characteristics in the solvent system used, thereby allowing ease of suspension in the reaction vessel. This ease of suspension or fluidization in the reaction vessel advantageously allows for quick mixing of reactants and, since certain reactants and/or intermediates are unstable, allows the reactions to go quickly to completion with improved yields resulting in high coupling efficiencies. These polymeric moieties are capable of being loaded with at least 10 μmoles/g nucleoside, preferably from about 10 μmoles/g to about 400 μmoles/g, more preferably from about 20 to about 80 μmoles/g. Suitable polymeric moieties exhibit improved efficiency of rinsing (and thus decreased adsorption of reagents and solvents to support) during the reaction cycle. These polymeric moieties are stable to contact with strong base such as ammonium hydroxide solutions used to release oligomers from supports and show no appreciable dissolution at high pH. Preferred are polymeric moieties which do not appreciably expand or contract (i.e. swell) in the solvents used in the reaction cycle, preferably such polymeric moieties exhibit less than a 100% change in volume (expansion or contraction) as solvents are changed during the reaction cycle. Suitable polymeric moieties exhibit resistance to attrition so that fewer fines are formed and are not friable or brittle so that they do not crumble or pulverize when fluidized or stirred in a reaction vessel. In addition, these polymeric moieties should be substantially inert and unreactive with reagents used for coupling procedures in oligomer synthesis.

These non-aromatic organic polymeric moieties have polymeric chains that contain less than about 10% aromatic residues, that is less than about 10% aromatic monomeric units within the polymeric chains, as opposed to the cross-links. These polymeric moieties may be prepared using aromatic cross-linking reagents such as divinylbenzene and, thus, may contain aromatic cross-links.

Preferred non-aromatic polymeric moieties include copolymers of a monoethylenically unsaturated aliphatic monomer and a polyethylenically unsaturated monomer. Suitable polyethylenically unsaturated monomers include polyethylenically unsaturated esters of methacrylic acid or acrylic acid and polyvinylidene monomers. Preferred monoethylenically unsaturated aliphatic monomers include aliphatic esters of acrylic acid or methacrylic acid. Preferred polyethylenically unsaturated monomers include substituted polyethylene esters or ethylene esters of acrylates. Preferred polyvinylidene monomers include divinylbenzene.

Thus, according to one aspect of the invention, preferred are non-aromatic organic polymeric moieties having one or more of the following characteristics: have a density such that it exhibits excellent fluidization in the solvent used; have a particle size of from about 10 to about 200 microns have a pore size of from about 60 Å to about 2,000 Å, preferably from about 300 Å to about 1500 Å; show a maximum change in volume with change of solvent of about 100% or less, and are not friable.

One class of preferred polymeric moieties comprise organic polymers which optionally have a macrorecticular structure. One group of preferred polymeric moieties may include those which comprise copolymers of a polyvinylidene cross-linking monomer and a monoethylenically unsaturated aliphatic ester of acrylic acid, especially those polymers produced by a process of suspension copolymerization in the presence of a liquid which is substantially immiscible with the aqueous phase of the suspension polymerization medium and which does not substantially swell the resulting copolymer. Other suitable polymers include polymeric products of homobifunctional vinyl cross-linking monomeric reagents such as divinylbenzene and/or substituted polyethylene esters of acrylic acid or methacrylic acid. Some of these preferred polymers are characterized by a reticular structure of microscopic channels through the mass of the polymer and having a density less than the same polymer composition without the reticular structure. Such polymers and processes for their preparation and use are disclosed in U.S. Pat. Nos. 4,224,415; 4,256,840; 4,297,220; 4,382,124; and 4,501,826, the disclosures of which are incorporated herein by reference. Especially preferred are hydroxylated methacrylic polymers.

Optionally, the polymeric moieties are derivatized (or "activated") to facilitate linking of the nucleosidyl moiety to the support by the linking moiety. Accordingly, the polymeric moiety preferably is derivatized or activated with a suitable reactive group which can act as a first conjugation partner; such groups include epoxy, hydroxyl, formyl, primary amino, carboxyl, trifluoromethane sulfonyl, trifluoroethyl sulfonyl and the like and other groups depicted as "—X" in FIGS. 6a and 6b.

One especially preferred class of polymeric moiety comprises derivatized methacrylic polymers, especially those derivatized with epoxy, formyl, carboxy or tresyl groups. Particularly suitable methacrylic polymers include those sold under the trade name AF Toyopearl® (TosoHaas, Philadelphia, Pa.). Particularly preferred is AF-Epoxy Toyopearl®. Another particularly suitable non-aromatic organic polymeric moiety is a copolymer of 2-hydroxyethylmethacrylate and ethylene dimethacrylate sold under the trade name HEMA (Alltech, Deerfield, Ill.).

B. PREFERRED LINKING MOIETIES

Suitable linking moieties include functionalized substantially straight chain alkylene groups or other spacer groups such as those disclosed by Katzhendler et al (Tetrahedron Letters 45(9): 2777–2792 (1989)). According to one preferred aspect, such linking moieties generally comprise from about 5 to about 80 carbon atoms, preferably from about 17 to about 35, more preferably from about 17 to about 21 carbon atoms. According to another especially preferred aspect, these linking moieties comprise from about 0 to about 40 carbon atoms, more preferably from about 2 to about 20 carbon atoms. Preferably such linking moieties have a functional group (or conjugation partner) at the end of the chain which is capable of reacting with another functional group to form a conjugation pair. Suitable functional groups (or conjugation partners, see FIGS. 6a and 6b) for the linking moiety include amino, hydroxyl, sulfhydryl, and like functional groups. Suitable linking moieties may include bifunctional compounds having substantially straight-chained alkylene groups separating the functional groups, such as alkylene diamines and alkylene diols. One preferred group of linking moieties includes alkylene diamines having a chain length of at least 5 carbon atoms, preferably from about 5 to about 50 carbon atoms and more preferably from about 6 to about 18 carbon atoms.

C. COUPLING MOIETIES

Figure 2:
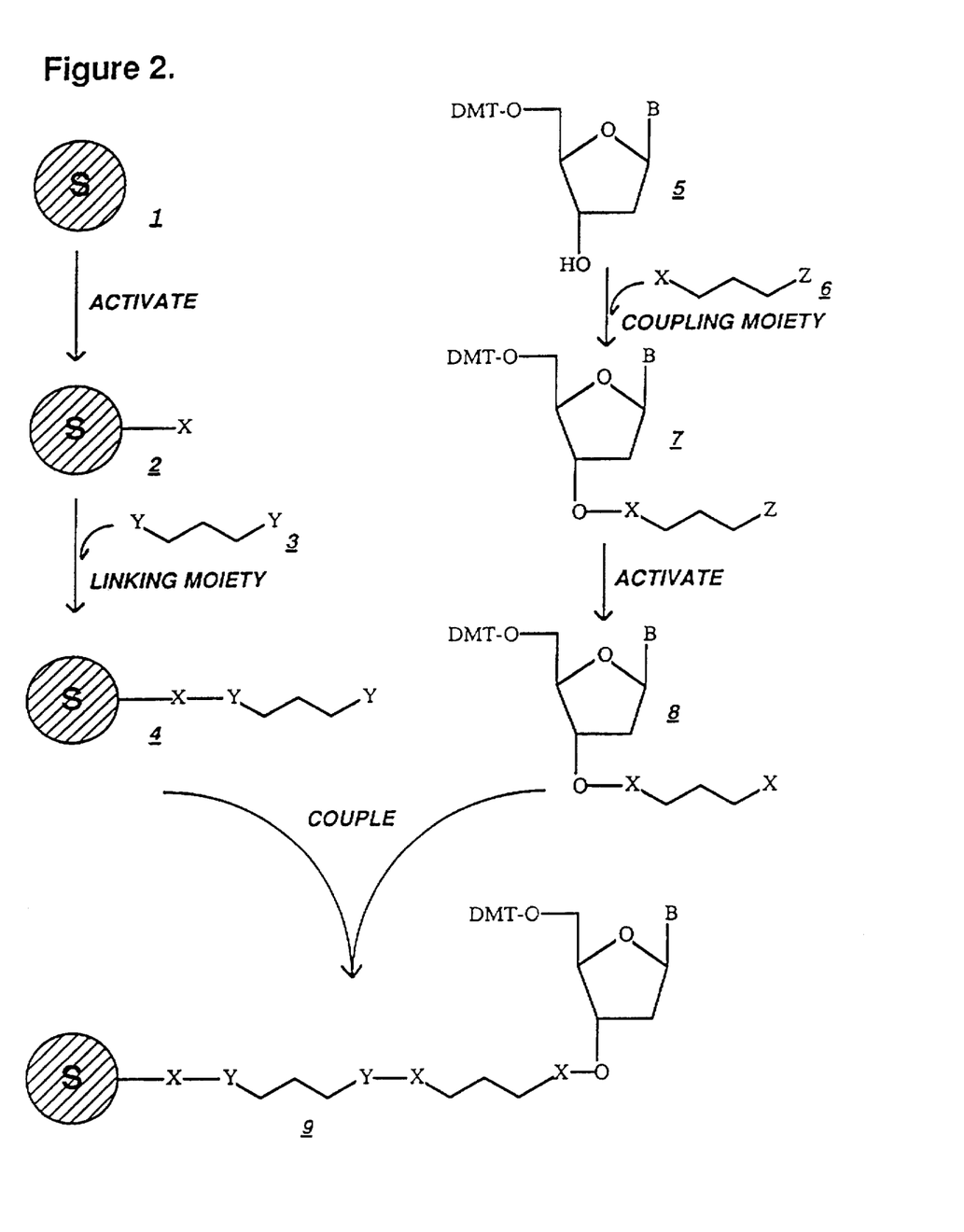
FIGS. 2 to 5 depict alternative general reaction schemes for preparation of the polymeric reagents of the present invention.
Figure 3:
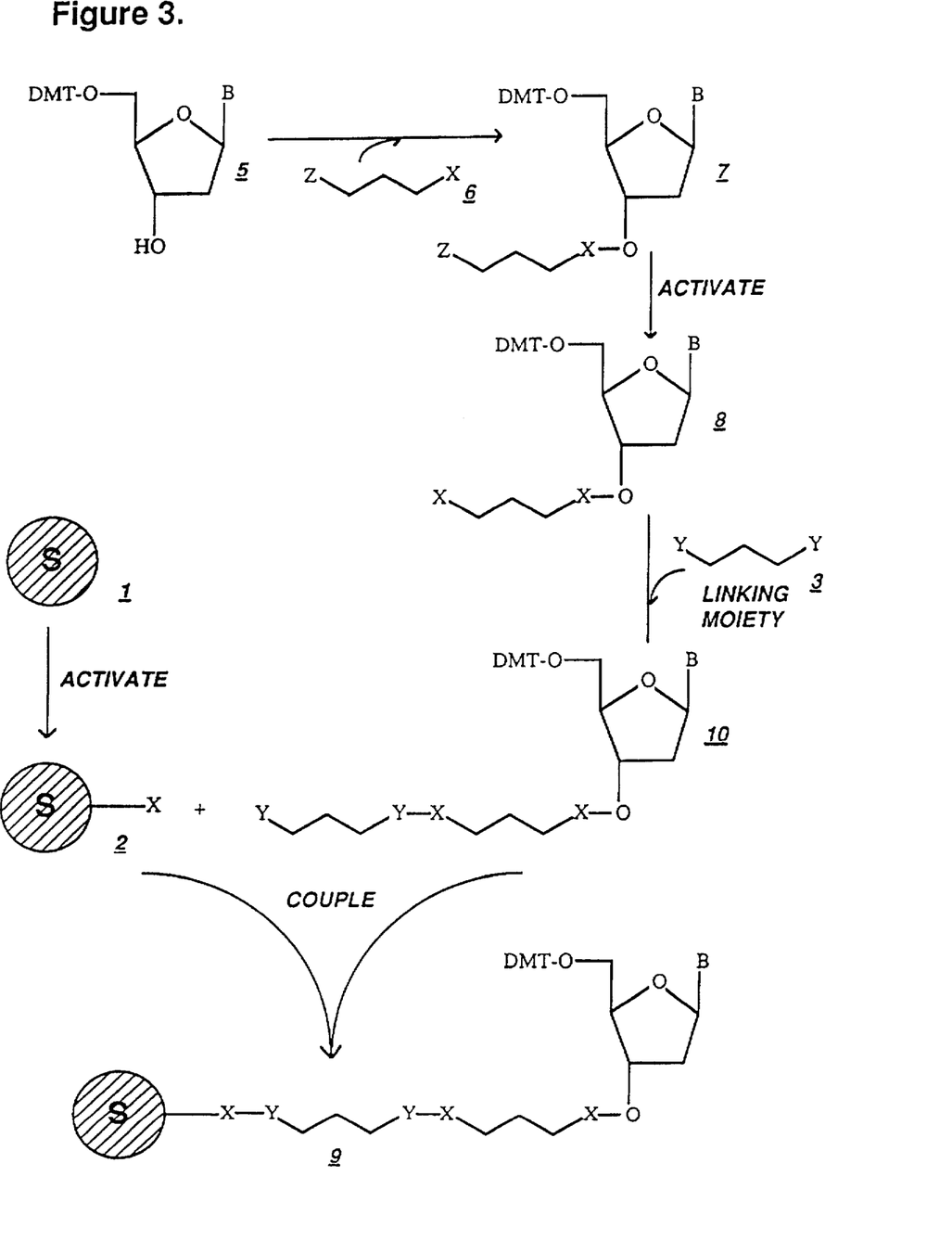
Figure 4:
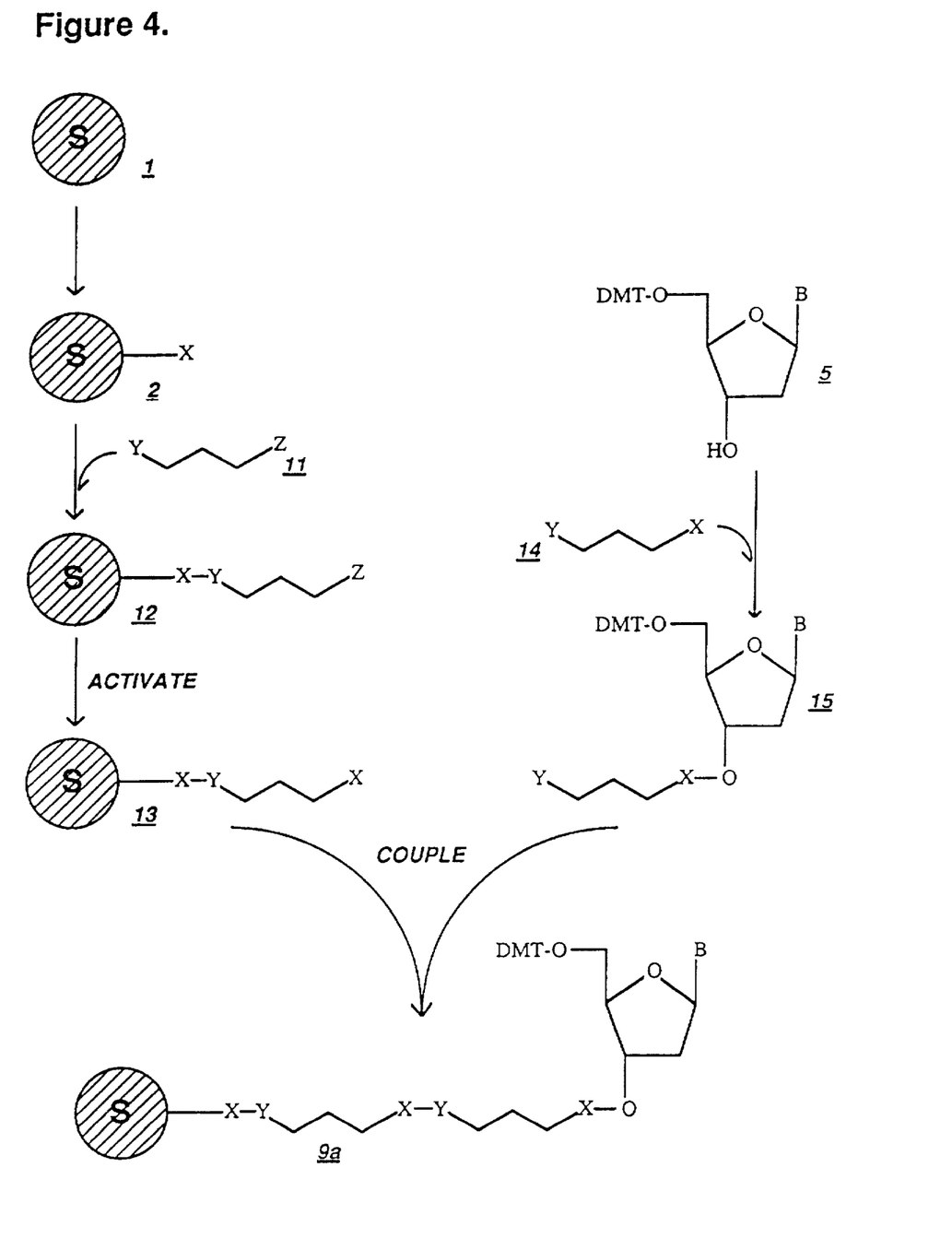

The polymeric moieties of the present invention may optionally include a coupling moiety which is conjugated to both the linking moiety and to the nucleosidyl moiety (see FIGS. 2 to 4). Suitable coupling moieties include straight or branched chain alkylene groups having two conjugation partners attached thereto. Suitable conjugation partners include those depicted in FIGS. 6a and 6b and which are capable of coupling the linking moiety to the nucleosidyl moiety by forming a conjugation pair with the linking moiety and the nucleosidyl moiety. Suitable coupling moieties generally comprise from about 1 to about 12 carbon atoms, more preferably from about 4 to about 6 carbon atoms.

D. PREFERRED NUCLEOSIDYL MOIETIES

Preferred are nucleosidyl moieties which have been functionalized (or "activated") at the 3'-O-position to have a conjugation partner, so as to be capable of reacting with a conjugation partner of a linking moiety or a coupling moiety to form a conjugation pair. Suitable functionalizing groups include succinyl, substituted carbonate, para-nitrophenoxy carbonate, diacids such as hexane, heptane or pentane dioic acids, those groups (—X, where —Y is —OH) listed in FIG. 6b and the like. These nucleosidyl moieties preferably have protecting groups attached to reactive substituents on the purine or pyrimidine base and are blocked at the 5'-O-position of the sugar ring with a blocking group such as di-(p-anisoyl)phenylmethyl ("Dimethyoxytrityl", "DMT" or "trityl"). Many suitable nucleosidyl moieties functionalized with a conjugation partner or having a coupling moiety attached thereto are commercially available.

E. PREPARATION OF POLYMERIC REAGENTS

According to one aspect, the polymeric reagents of the present invention are conveniently prepared by mixing the polymeric moiety (support) with a linking moiety so that the polymeric moiety and linking moiety are coupled to give a support-linking moiety complex. The linking moiety is typically a bifunctional substantially straight chained molecule such as an alkylene diamine or diol or alternatively may comprise a molecule having polyglycine or polyureido groups (such as those disclosed by Katzhendler et al., Tetrahedron 45(9):2777–2792 (1989)) or conjugation partners such as those depicted in FIGS. 6a and 6b. When alkylene diamines or diols are used, preferably an excess is employed to decrease cross-linking of the polymeric moiety with itself. Then, the polymeric-linking complex is contacted with the functionalized nucleosidyl moiety, optionally having a coupling moiety coupled thereto, so that the nucleosidyl moiety is coupled to of the linking moiety portion of the support-linking moiety complex.

After coupling of the polymeric-linking complex to the nucleosidyl moiety, unreacted derivatizing or functional groups or uncoupled conjugation partners are rendered unreactive by a capping reaction. (See e.g. Example 1).

The resulting polymeric reagent may then be used as a support for the solid phase synthesis of oligomers using standard chemistries for the preparation of such oligomers.

Also, these polymeric reagents are especially suitable for use as supports in the synthesis of oligomers by the improved methods disclosed and claimed in our commonly-assigned and concurrently filed patent application, "Improved Process for the Synthesis of Oligomers," the disclosure of which is incorporated herein by reference.

FIGS. 2 to 5 depict examples of alternative general synthesis schemes for the preparation of polymeric reagents of the present invention. Examples of first conjugation partner —X and second conjugation partner —Y and the conjugation pair, —XY— formed thereby are depicted, in FIGS. 6a and 6b.

E (1) FIG. 2

In the reaction scheme depicted in FIG. 2, a support-linking moiety complex is coupled to an activated nucleosidyl moiety. Thus, the polymeric moiety (or support) 1, is activated to give activated support, 2, having a first conjugation partner. Activated support, 2, is contacted with linking moiety, 3, having a second conjugation partner, under conditions so that the first and second conjugation partners form a conjugation pair, to give support-linking moiety complex 4.

The 5'-blocked nucleoside, 5, is contacted with coupling moiety, 6, having a first conjugation partner, —X, to form a nucleosidyl moiety, 7, having a linkage, —OX—, which is cleavable under non-adverse conditions. Nucleosidyl moiety, 7, is activated to give activated nucleosidyl moiety, 8.

Complex 4 and activated nucleosidyl moiety 8 are contacted under conditions that the first conjugation partner of 8 and the second conjugation partner of 4 couple to form a conjugation pair, to give polymeric reagent 9.

E (2) FIG. 3

According to the reaction scheme depicted in FIG. 3, a nucelosidyl-linking moiety complex, 10, is coupled to activated support (polymeric moiety) 2. Thus, 5'-blocked nucleoside 5 is contacted with coupling moiety 6 having a first conjugation partner, —X, to form a linkage, —OX— which is cleavable under non-adverse conditions, giving nucleosidyl moiety 7. Nucleosidyl moiety, 7 is activated to give activated nucleosidyl moiety 8 having a free first conjugation partner. Activated nucleosidyl moiety 8 is contacted with linking moiety 3 having a second conjugation partner under conditions so that first and second conjugation partners form a conjugation pair to give nucleosidyl-linking moiety complex, 10. Complex 10 having a free second conjugation partner is contacted with activated polymeric moiety 2 having a free first conjugation partner under conditions that the first and second conjugation partners form a conjugation pair, to give polymeric reagent 9.

E (3) FIG. 4

In the reaction scheme depicted in FIG. 4, support-linking moiety complex 12 is prepared, then activated, to give activated complex 13 and then coupled with an activated nucelosidyl moiety 15 as follows.

Support (or polymeric moiety), 1, is activated to give activated support 2 having a free first conjugation partner, —X. Activated support 2 is contacted with unactivated linking moiety 11 having a free second conjugation partner to give support-linking moiety complex 12. Complex 12 is then activated to give activated complex 13 having a free first conjugation partner.

The 5'-blocked nucleoside 5, is contacted with coupling moiety 14 having a free first conjugation partner to form a nucleosidyl moiety 15 having a linkage —OX— which is clearable under non-adverse conditions and a free second conjugation partner.

Activated complex 13 and nucleosidyl moiety 15 are contacted under conditions that the first conjugation partner of 13 and the second conjugation partner of 15 couple to form a conjugation pair, to give polymeric reagent 9a.

Figure 5:
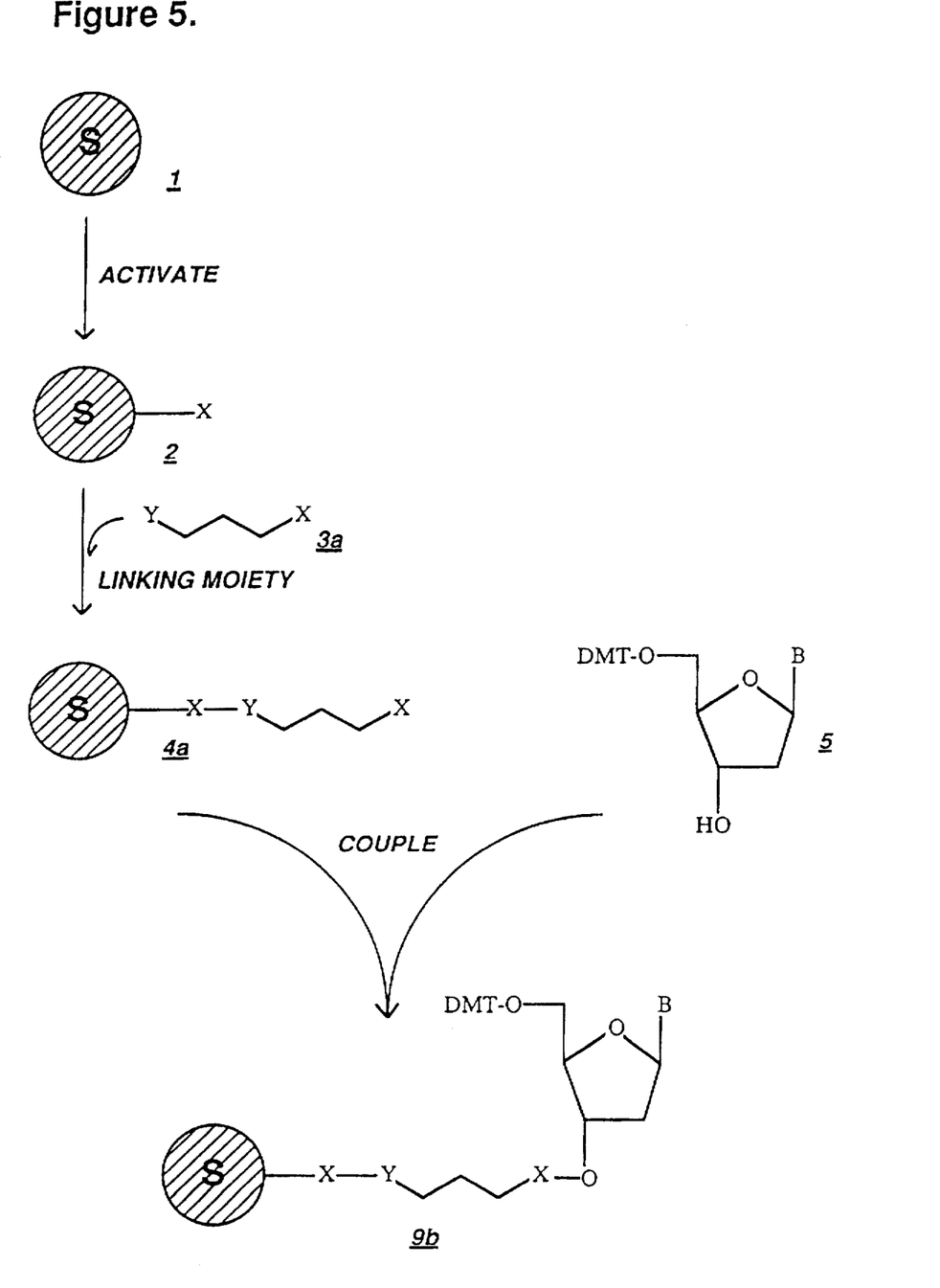

E (4) FIG. 5

The reaction scheme of FIG. 5 depicts preparation of polymeric reagents according to the present invention without the optional coupling moiety so, that a conjugation partner of the linking moiety forms a conjugation pair with a conjugation partner attached to the 3'-oxygen of the 5'-blocked nucleoside 5.

Thus, polymeric moiety (support) 1 is activated to give activated support 2, having a first conjugation partner. Activated support 2 is contacted with linking moiety 3a, having a second conjugation partner, under conditions so that the first and second conjugation partners form a conjugation pair, to give support-linking moiety complex 4a.

The 5'-blocked nucleoside, 5, is reacted with complex 4a to give polymeric moiety 9b wherein —OX— is a linkage which is cleavable under non-adverse conditions.

F. UTILITY

As noted, the polymeric reagents of the present invention are particularly useful in the solid phase synthesis of oligomers.

Figure 1:
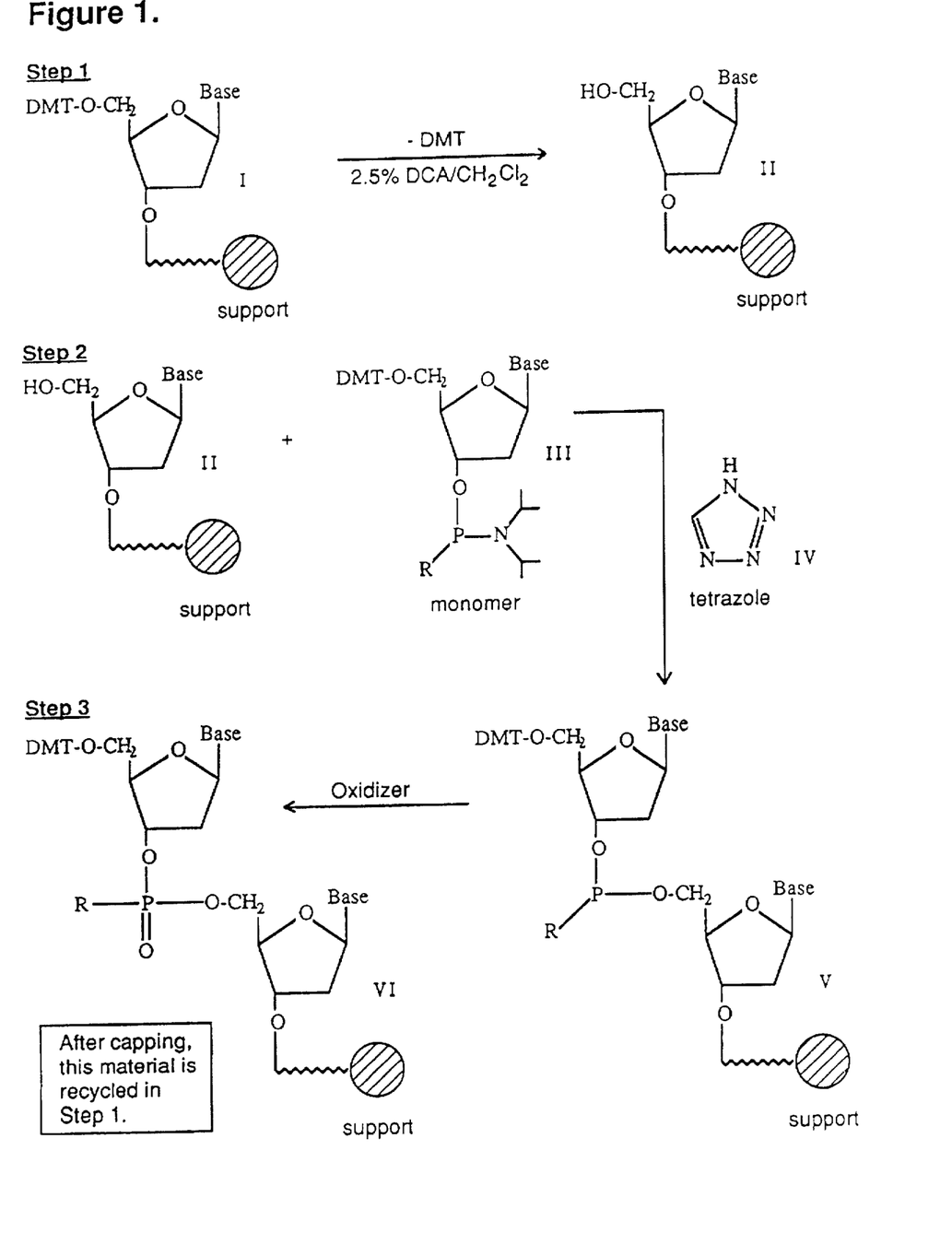
FIG. 1 depicts a general reaction scheme for the solid phase synthesis of oligomers using the polymeric reagents of the present invention.
Figure 1D:
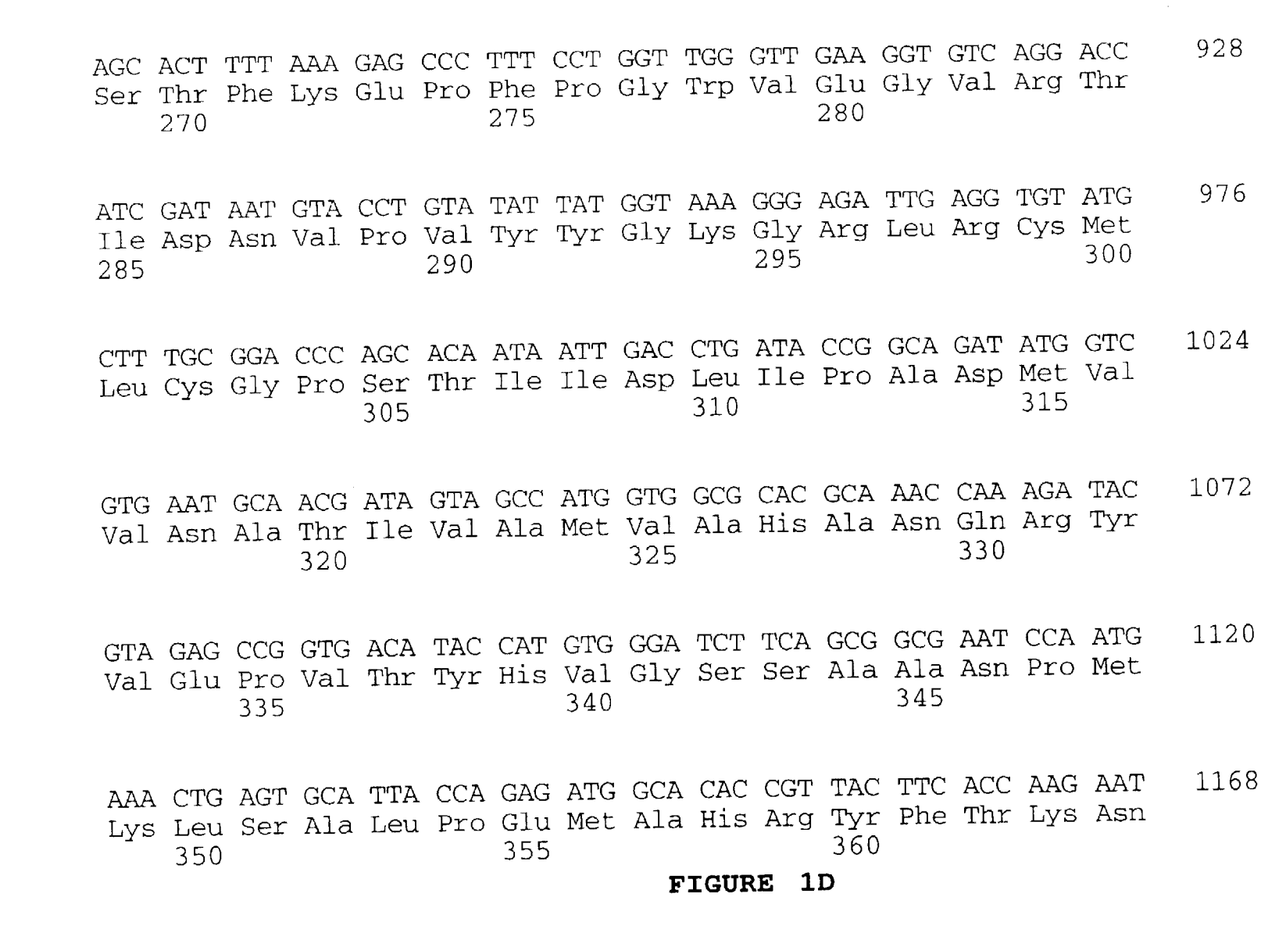

The general reaction scheme for synthesizing oligomers involves a multicycle process of forming internucleotide phosphorous linkages between a monomer and the polymeric reagent or growing oligomer chain (see FIG. 1). Nucleosides are progressively added, one per cycle, to a growing chain starting with the polymeric reagent until the desired chain length is reached.

The basic solid phase process of forming a phosphorus-containing internucleoside linkage is depicted in FIG. 1 and includes four steps: (a) deblocking of the 5'-hydroxyl of the first nucleoside ("detritylation"); (b) adding a second nucleoside ("monomer" in FIG. 1) to the reaction mixture having a first nucleoside in the presence of an activator under coupling and activating conditions, so that the second nucleoside "couples" or "condenses" with the first nucleoside to give an internucleoside linkage having a trivalent phosphorus group; (c) oxidizing the trivalent phosphorus group to a pentavalent phosphorus group using an oxidizer reagent; and (d) capping unreacted (or uncoupled) 5'-hydroxyl groups on the first nucleoside to prevent unwanted chain extension in subsequent cycles.

To assist in understanding the present invention, the following examples are included which describe the results of a series of experiments. The following examples related to this invention should not, of course, be construed as specifically limiting. The invention and such variations of the invention, now known or later developed, which would be within the purview of one skilled in the art are considered to fall within the scope of the present invention as hereinafter claimed.

EXAMPLES

Example 1

DERIVATIZATION OF HYDROXYLATED METH-ACRYLIC POLYMER AS A SOLID SUPPORT FOR DNA SYNTHESIS

Into a 2 liter flask fitted with an overhead stirrer was added hydroxylated methacrylic polymer beads (100 g, 1000 Å pore size, 40–90 µm particle size) (Toyopearl®, TosoHaas, Philadelphia, Pa.) derivatized with epoxide groups (812 µeq/g). To this was added 1,12-dodecanediamine (100 g) and 1 liter of 1,4-dioxane. The mixture was stirred and refluxed for 18 hours. The mixture was then filtered warm and the solids washed with warm dioxane (300 ml). The solid material was washed with dichloromethane and air dried. The solid was suspended in a 2.5% solution of dichloracetic acid in dichloromethane and shaken on a shaker table for 4 hours. The mixture was filtered and washed with dichloromethane. The solid was then washed with a 15% solution of triethylamine in dichloromethane (1 liter) followed by a wash with dichloromethane (300 ml) and finally air dried. A portion of this material (25 g) was suspended in dry pyridine (1250 ml). To this was added 5'-O-dimethyoxytrityl-N-isobutyryl-3'-O-succinyl-2'-deoxyguanosine 1 (4.0 g), ethyl-3(3-dimethylamino)propyl carbodiimide hydrochloride (10.0 g), 4-dimethylaminopyridine (500 mg), and triethylamine (2 ml). The mixture was shaken on a shaker table for 60 hours. The mixture was filtered and washed with pyridine (300 ml), methanol (300 ml), and dichloromethane (300 ml). The material was air dried. The loading of nucleoside on support was determined by measuring trityl release of a small aliquot in 2.5% dichloracetic acid in dichloromethane at 504 nm in a spectrophotometer. The loading in this example was 57.4 µmoles/g.

The material was suspended in acetic anhydride-pyridine (1/1) and 4-dimethylaminopyridine (300 mg) added. After stirring 4 hours the material was filtered and washed with dichloromethane and dried in vacuo. The material was then ready for use on the DNA synthesizer.[1]

[1] Richard T. Pon, Nassim Usman, and Kelvin K. Ogilvie Biotechniques 6 768–775 (1988).

Example 2

SYNTHESIS OF AN OCTADECAMER ON A 150 µMOLE SCALE USING LOW WATER OXIDIZER REAGENT

Non-aromatic organic polymeric moiety (2.44 g) (Toyopearl®, TosoHaas Philadelphia, Pa.) derivatized with 5'-O-DMT-N-isobutyryl 3'-O-succinyl deoxycytidine (61.5 µmoles/g) was placed in the reactor vessel of a Biosearch 8800 DNA synthesizer. This solid support was treated with 5×14.6 ml aliquots of 2.5% dichloracetic acid in dichloromethane. The bright orange colored solution was collected for later spectrophotometric analysis. The support was then washed with 7×17.5 ml aliquots of dry acetonitrile. To the support was added 4 ml of a solution of N-isobutyryl-5'-O-DMT-2'-O-deoxyguanosine methylphosphonomidite monomer at a concentration of 100 mM (400 µmoles, 2.7 equivalents). While stirring, tetrazole (1.98 ml, 894 µmoles, 450 mM concentration, 2.24 equivalents with respect to monomer) was added. The mixture was allowed to stir for 3 minutes followed by filtration and 2×2.8 ml washes with acetonitrile. Oxidizer (4.06 ml, 2.7 equivalents with respect to support loading, oxidizer=25 g/l I$_2$, 0.18% water, 25% 2,6-lutidine, 74.82% tetrahydrofuran) was added. This was allowed to stir for 1 minute and was subsequently filtered and washed with 4×18 ml of dry acetonitrile. The material on the support was then treated with the concomitant addition of Cap A solution (10 ml, 40% acetic anhydride, 60% tetrahydrofuran) and Cap B solutions (10 ml, 0.625% 4-dimethylaminopyridine in anhydrous pyridine). This mixture was allowed to stir for 1 minute. The mixture was filtered and the support washed with 6×18 ml portion of acetonitrile. At this point the cycle was repeated starting with the removal of the DMT group on the deoxyguanosine nucleoside which had just been added to the deoxycytidine already linked to the support with 2.5% dichloroacetic acid in dichloromethane solution. The 5'-hydroxyl was then free for reaction with the next monomer which was 5'-O-DMT-thymidine. The above process was repeated 15 more times with the appropriate monomer to obtain an oligomer of the sequence: 5'GTC-TTC-CTG-CCC-CAT-TGC-3'.

Example 3

COMPARISON OF FIRST COUPLING YIELDS OF POLYMERIC REAGENT AS SUPPORT TO CONTROLLED PORE GLASS SUPPORT

First coupling reactions were carried out as described in Example 2 using as the support either a polymeric reagent of the present invention (prepared according to methods such as that described in Example 1) and, conventional controlled pore glass (CPG) support. Coupling efficiencies were measured spectrophotometrically by trityl release as described in Example 1.

The coupling efficiencies are reported below:

| CPG | | Polymer | |
|---|---|---|---|
| RDO-558 | | RDO-579 | |
| G on support- | 1.1803 AU[2] | G on support- | 1.5678 AU |
| G first coupling- Yield-130.4% | 1.5389 AU | T first coupling- Yield-99.9% | 1.5670 AU |
| RDO-557 | | RDO-628 | |
| G on support- | 1.0971 AU | A on support- | 1.9075 AU |
| G first coupling- Yield-155% | 1.7020 AU | T first coupling- Yield-98.6% | 1.8815 AU |

[2] "absorbance units"

The above comparison demonstrates that, when used as a support for oligomer synthesis, the CPG has more than about 30% of the oligomer chains growing with the wrong starting base, that is by initiating a new oligomer chain by coupling directly to the CPG, not to the nucleoside attached to the CPG. This non-specific initiation results in oligomers of improper chain length, in particular oligomers that will be N-1 in length, where N is the intended length of the oligomer synthesized. Thus, if the desired oligomer length is 18, then these N-1 chains will result in oligomers that are 17 nucleosides in length.

Example 4

SYNTHESIS OF PHOSPHOROTHIOATE 15-MERS

Solid support (2.61 g) (Toyopearl®, TosoHaas, Philadelphia, Pa.) derivatized with 5'-O-DMT-N-benzoyl 3'-O-succinyl-2'- deoxyadenosine (76.7 μmoles/g) was placed in the reactor vessel of a Milligen Biosearch 8800 DNA synthesizer. The phosphorothioate oligomer was synthesized according to the procedure described by Iyer and coworkers (Iyer, R. P., et al., J. Am. Chem. Soc. 112:1253–1254 (1990)), by successively coupling the appropriate B-cyanoethyl monomers (Milligen or Glen Research) in the desired order. The Milligen program for diester synthesis was used with the exception that a 100 mM solution of Beaucage reagent (3H-1,2-benzo-dithiole-3-one 1, 1-dioxide) in acetonitrile was used in place of the iodine/water oxidizing reagent normally used in DNA synthesis. The Beaucage reagent was used to introduce the sulfur atom onto the phosphorus to give the phosphorothioate linkage.

In one synthesis, using the above polymeric reagent and run on a 200 μmole scale, a phosphorothioate oligomer having the sequence:

TCT-CTA-GCA-GAG-GAA was prepared with an average coupling efficiency of 95.7%.

In a second synthesis, using the polymeric reagent noted above, also run on a 200 μmole scale, a phosphorothioate oligomer having the sequence:

TTC-TGA-GGC-CGT-GTA was prepared with an average coupling efficiency of 96.8%.

---

We claim:

1. A polymeric reagent for solid phase synthesis of oligomers which has a particulate polymeric moiety linked by a linking moiety to a nucleosidyl moiety wherein:

(a) said polymeric moiety is a polymer which has cross-linked polymeric chains wherein the polymeric chains have from 0% to no more than 10% aromatic monomeric units and at least about 90% to 100% non-aromatic monomeric units within the polymeric chains and optionally have aromatic cross-links and which is derivatized with a reactive group —$X_1$ which is selected from —X groups depicted in FIGS. 6a and 6b and wherein said polymer shows a maximum change in volume with change in solvent of less than about 100%;

(b) said linking moiety is a bifunctional compound of formula $Y_1$-alk-$Y_2$ wherein alk is a substantially straight-chained alkylene group of 5 to 80 carbon atoms and $Y_1$ and $Y_2$ are selected from —Y groups depicted in FIGS. 6a and 6b;

(c) said nucleosidyl moiety is activated at its 3'—OH to have a —$X_2$ group which is selected from —X groups depicted in FIGS. 6a and 6b; and (d) each of —$X_1$ and $Y_1$ and —$X_2$ and $Y_2$ are selected to give —$X_2Y_2$—groups selected from the —XY— groups depiected in FIGS. 6a and 6b.

2. A polymeric reagent according to claim 1 wherein polymeric moiety has a particle size of about 10 to about 100 microns and a pore size of about 60 Å to about 2.000 Å.

3. A polymeric reagent according to claim 2 wherein said polymer is a hydroxylated methacrylic polymer.

4. A polymeric reagent according to claim 2 wherein said linking moiety is an alkylene diamine of about 5 to about 50 carbon atoms.

5. A polymeric reagent according to claim 4 wherein said linking moiety is an alkylene diamine of about 6 to about 18 carbon atoms.

6. A polymeric reagent according to claim 5 wherein said polymeric moiety is a methacrylic polymer.

7. A polymeric reagent according to claim 5 wherein said polymer is a hydroxylated methacrylic polymer.

8. A polymeric reagent according to claim 6 wherein said polymeric moiety is a methacrylic polymer.

9. A polymeric reagent according to claim 1 wherein said polymeric moiety is a copolymer of monoethylenically unsaturated aliphatic monomer selected from aliphatic esters of acrylic and of methacrylic acid and a polyethylenically unsaturated monomer selected from polyethylenically unsaturated esters of methacrylic acid, polyethylenically unsaturated esters of acrylic acid, and polyvinylidene monomers.

10. A polymeric reagent according to claim 9 wherein said polyethylenically unsaturated monomer is a polyvinylidene cross-linking monomer.

11. A polymeric reagent according to claim 10 wherein said polyvinylidene cross-linking monomer is divinylbenzene.

12. A polymeric reagent according to claim 10 wherein said monoethylenically saturated aliphatic monomer is an aliphatic ester of acrylic acid or an aliphatic ester of methacrylic acid.

13. A polymeric reagent according to claim 11 wherein said monoethylenically saturated aliphatic monomer is an aliphatic ester of acrylic acid or an aliphatic ester of methacrylic acid.

14. A polymeric reagent according to claim 9 wherein said polyethylenically unsaturated monomer is an ester of acrylic acid or an ester of methacrylic acid.

15. A polymeric reagent according to claim 14 wherein said monoethylenically saturated aliphatic monomer is an aliphatic ester of acrylic acid or an aliphatic ester of methacrylic acid.

16. A polymeric reagent according to claim 9 wherein said monoethylenically unsaturated aliphatic monomer is 2-hydroxyethyl methacrylate.

17. A polymeric reagent according to claim 16 wherein said polyethylenically unsaturated monomer is ethylene dimethacrylate.

18. A polymeric reagent for solid phase synthesis of oligomers which has a particulate polymeric moiety linked by a linking moiety to a nucleosidyl moiety wherein (a) said polymeric moiety has a particle size of from about 10 to about 200 microns, has a pore size of from about 60 Å to about 2.000 Å, has a macroreticular structure and is selected from methacrylic polymers derivatized with a reactive group —$X_1$ which is selected from the X groups of FIGS. 6a and 6b;

(b) said linking moiety is a bifunctional compound of formula $Y_1$-alk-$Y_2$ wherein alk is a substantially straight chained alkylene group of 5 to 80 carbon atoms and $Y_1$ and $Y_2$ are selected from —Y groups of FIGS. 6a and 6b; and (c) said nucleosidyl moiety is activated at its 3'—OH to have a group —$X_2$ which is selected from the X groups of FIGS. 6a and 6b;

wherein $X_1$ and $Y_1$ are selected so as to react to form a conjugation pair —$X_1Y_1$— which is selected from —XY— groups depicted in FIGS. 6a and 6b and $X_2$ and $Y_2$ are selected so as to react to form a conjugation pair —$X_2Y_2$— which is selected from —XY groups depicted in FIGS. 6a and 6b.

19. A polymeric reagent according to claim 18 wherein $X_1$, $X_2$, $Y_1$, $Y_2$ are selected from the groups below:

(a) if $Y_1$ or $Y_2$ is —SH, then $X_1$ or $X_2$ and the product —$X_1Y_1$— or —$X_2Y_2$— are as follows:

| $-X_1$ or $-X_2$ | $-X_1Y_1-$ or $-X_2Y_2-$ |
|---|---|
| X–CH₂–C(=O)– | –S–CH₂–C(=O)– |
| X–CH₂–C(=O)–NH– | –S–CH₂–C(=O)–NH– |
| R–S–S– | –S–S– |
| maleimide (N–) | succinimide-S (N–) |
| Hg–C₆H₄– | –S–C₆H₄– |

(b) if $Y_1$ or $Y_2$ is $-NH_2$, then $X_1$ or $X_2$ and the product $-X_1Y_1-$ or $-X_2Y_2-$ are as follows:

| $-X_1$ or $-X_2$ | $-X_1Y_1-$ or $-X_2Y_2-$ |
|---|---|
| RO–C(=O)– | –NH–C(=O)– |
| CH₃O–C(=NH₂⁺)– | –N(H)–C(=NH₂⁺)– |
| H–C(=O)– | –N=C– |
| X–C(=O)– | –NH–C(=O)– |
| epoxide | –NH–CH₂CHOH– |
| aziridine (N) | –NH–CH₂CHNH₂– |
| SCN– | –NH–C(=S)–NH– | and (c) if $Y_1$ or $Y_2$ is $-OH$, then $X_1$ or $X_2$ and the product $-X_1Y_1-$ or $-X_2Y_2-$ are as follows:

| $-X_1$ or $-X_2$ | $-X_1Y_1-$ or $-X_2Y_2-$ |
|---|---|
| X–C(=O)– | –O–C(=O)– |
| RO–C(=O)– | –O–C(=O)– |
| epoxide | –O–CH₂CHOH– | wherein X is halogen and R is an organic radical.

20. A polymeric reagent according to claim 19 wherein said —$X_1$ is epoxide, —$Y_1$ and $Y_2$ are amino and —$X_2$ is ethyl-3-dimethylaminopropyl carbodiimide.

21. A polymeric reagent according to claim 20 wherein said polymeric moiety is a copolymer of 2-hydroxyethylmethacrylate and ethylene dimethacrylate.

* * * * *